United States Patent [19]

Scheiffele

[11] Patent Number: 5,661,154

[45] Date of Patent: *Aug. 26, 1997

[54] OXYPURINOL ALKALI AND ALKALINE EARTH SALTS IN AMORPHOROUS OR CRYSTALLINE FORM AS AGENTS FOR TREATING HYPERURICAEMIA AND GOUT

[75] Inventor: Ekkehard Scheiffele, Berlin, Germany

[73] Assignee: Henning Berlin GmbH Chemie-Und Pharmawerk, Berlin, Germany

[*] Notice: The term of this patent shall not extend beyond the expiration date of Pat. No. 5,430,037.

[21] Appl. No.: 383,939

[22] Filed: Feb. 6, 1995

Related U.S. Application Data

[63] Continuation of Ser. No. 5,403, Jan. 19, 1993, Pat. No. 5,430,037, which is a continuation of Ser. No. 671,743, May 7, 1991, abandoned.

[30] Foreign Application Priority Data

Nov. 25, 1988 [DE] Germany .................. 38 39 826.5

[51] Int. Cl.$^6$ ............................................. A61K 31/52
[52] U.S. Cl. ................................................ 514/262
[58] Field of Search ................................ 514/262

[56] References Cited

U.S. PATENT DOCUMENTS

| 3,624,205 | 11/1971 | Hitchings et al. ........... 514/262 |
| 5,368,864 | 11/1994 | Lahr et al. ................... 424/489 |
| 5,430,037 | 7/1995 | Scheiffele ..................... 514/262 |

FOREIGN PATENT DOCUMENTS

| 0237348 | 9/1987 | European Pat. Off. . |
| 975850 | 11/1964 | United Kingdom . |

OTHER PUBLICATIONS

Handbook of Pharmaceutical Excipients (1986), pp. 138–140.

Martindale, The Extra Pharmacopoeia, 28th Ed. (1982), pp. 417–419.

Lachman et al. "The Theory and Practice of Industrial Pharmacy", 2nd edition, pp. 99–104 1976.

Primary Examiner—Raymond Henley, III
Attorney, Agent, or Firm—Jacobson, Price, Holman & Stern, PLLC

[57] ABSTRACT

Treatment of hyperuricaemia and gout is possible by agents, among usual carriers and adjuvants containing pharmakologically active doses of oxypurinol alkali and/or alkaline earth salts in amorphous or crystalline form.

11 Claims, No Drawings

OXYPURINOL ALKALI AND ALKALINE EARTH SALTS IN AMORPHOROUS OR CRYSTALLINE FORM AS AGENTS FOR TREATING HYPERURICAEMIA AND GOUT

This application is a continuation of U.S. application Ser. No. 08/005,403 filed Jan. 19, 1993, now U.S. Pat. No. 5,430,037 which is a continuation application of U.S. application Ser. No. 07/671,743 filed May 7, 1991 now abandoned.

Therapy of hyperuricaemia and gout may be carried out using uricostatic or uricosuric agents or a combination of an uricostatic and an uricosuric agent. Generally, the xanthine oxidase inhibitors allopurinol or thiopurinol are being used as uricostatic agents; and as uricosuric agents, sulfinpyrazone and benzbromarone are primarily used. Investigations concerning the mechanism of action of allopurinol revealed that allopurinol has little activity itself, but that itstherapeutic effect is achieved only after metabolizing to give 4,6-dihydroxypyrazolo[3,4-d]pyrimidine (oxypurinol). Allopurinol and oxypurinol are inhibiting the enzyme xanthine oxidase equally strongly. However, the residence time of allopurinol within the organism—being well resorbable from appropriate galenic formulations upon peroral application—is only about 6 hours; thereafter, the major portion has been transformed to oxypurinol, part of it is metabolized to allopurinol 1-riboside, and a further 3 to 10% is excreted via kidneys. In comparison, oxypurinol has a half-life of about 22 hours, and, therefore, is the intrinsically active principle in an allopurinol therapy, while allopurinol has to be regarded as a prodrug. It would be a substantial progress and a great advantage, if one could succeed in using oxypurinol itself for gout therapy.

For this reason, many attempts have been made to administer the intrinsically active substance, oxypurinol, instead of the prodrug allopurinol. However, failure was encountered, because no success was achieved in finding a galenic formulation being sufficiently resorbable per os. Thus, Elion et al. (Renal Clearance of Oxypurinol, The Chief Metabolite of Allopurinol, American Journal of Medicine, Vol. 45, July 1968) had already carried out such experiments, though with negative results; also cf. Chalmers et al., Clin. Sci. 35, 353–362 (1968).

Even by using oxypurinol in micronized form, no practicable form of drug could be created.

It is known from German Offenlegungsschrift 37 07 999 to use oxypurinol for reducing cell damages after ischaemia and prior to reperfusion, by intravenous administration of an alkai metal salt, particularly the sodium salt. However, from the examples it can be seen that not the pure sodium salt was used, but a mixture of salt and excess sodium hydroxide solution. This follows especially from the pH values of about 1 to 2% solutions, being 11.5 or 12.0. The sodium salt having been prepared by the applicant in pure and crystalline form for the first time has a pH value of 9.7 in 5% aqueous solution, and crystallizes as the monohydrate.

The problem of using oxypurinol effectively in the treatment of hyperuricaemia and gout was now solved in a surprisingly simple way, by converting oxypurinol to its alkali and alkaline earth salts, and administering same in amorphous or crystalline form per os.

Thus, subject matter of the present invention are agents for peroral treatment of hyperuricaemia and gout, among usual carriers and adjuvants containing pharmacologically active doses of oxypurinol alkali and/or alkaline earth salts in amorphous or crystalline form. Preferably, said agents contain from 50 to 500 mg of active substance per dose unit.

Another subject matter of the invention is the use of oxypurinol alkali and/or alkaline earth salts in amorphous or crystalline form for the preparation of agents for peroral treatment of hyperuricaemia and gout.

Finally, subject matter of the invention is a method for peroral treatment of hyperuricaemia and gout by application of pharmaclologically active doses of oxypurinol alkali and/or alkaline earth salts in amorphous or crystalline form.

The preparation of said agents for peroral treatment of hyperuricaemia and gout is carried out in such way that first of all, oxypurinol is converted in a per se known manner to its alkali and alkaline earth salts, and these, together with usual carriers or adjuvants, are filled in amorphous or crystalline form into orally applicable medicaments such as tablets or capsules.

Comparative examinations of agents according to the invention and agents being based on micronized oxypurinol revealed that the resorption rate was increased by a factor of 3. An examination of the serum oxypurinol level after application of the agent according to the invention, as compared to the agents containing allopurinol, revealed that the relative resorption rate of sodium oxypurinol in comparison to oxypurinol from allopurinol is 87%. A comparative examination of allopurinol and agents according to the invention containing sodium oxypurinol revealed that the decrease of the serum uric acid level is comparable. Thus, it is possible to applicate an equimolar quantity of sodium oxypurinol instead of allopurinol, achieving the same therapeutic effect without stressing the body by-the other metabolites of allopurinol.

The invention is more fully explained in the following examples.

EXAMPLE 1

Sodium Oxypurinol

In a mixture of 25 l of pure methanol and 2.6 l of deionized water, 1 kg of dry oxypurinol is suspended, and within 1 h a solution of 525 g NaOH, pure, and 4.725 l of deionized water is added with stirring. A crystal slurry is formed, which is separated after a 3 hour period of stirring by filtering or suction filtering, washed with 10 l of pure methanol in portions, and dried at 60° C.

Yield about 95% of sodium oxypurinol.

Properties of Sodium Oxypurinol

Empirical formula: $C_5H_3N_4O_2Na.H_2O$

MW 192.1

Said sodium salt is monosodium oxypurinol monohydrate. The salt is white and crystallizes in fine needles. In aqueous solution, it reacts alkaline, and a 5% solution has a pH value of 9.7. its solubility is:

in water at 25° C. 15.8 g/l 0° C. 7.2 g/l;

in methanol/water (3:1 by vol.) at 25° C. about 2.0 g/l.

The salt is stable on air and endures drying temperatures up to about 70° C. From its hot solution, oxypurinol can be precipitated almost quantitatively with diluted hydrochloric acid (10%).

EXAMPLE 2

Potassium Oxypurinol

As in example 1, oxypurinol is suspended in 90% methanol, and accordingly reacted with 735 g of KOH.

Yield about 85% of potassium oxypurinol.

EXAMPLE 3

Magnesium Oxypurinol

The aqueous suspension of pure oxypurinol (2 moles) with 1 mole magnesium chloride is reacted with an excess of strongly basic ion exchange resin (e.g. Amberlite IRA 400 or DOWEX 1 SBR) at about 60° C. with stirring, the resin is separated, and after evaporation the magnesium salt is precipitated with isopropanol. The magnesium salt is obtained in amorphous form.

EXAMPLE 4

Sodium Oxypurinol Tablets 113.7 g of sodium oxypurinol according to example 1 are mixed dryly with 30 g of microcrystalline cellulose, 6.0 g of cross-linked polyvinylpyrrolidone, and 2.1 g of polyvinylpyrrolidone (average molecular weight about 25,000), wetted with water, the resulting granulate is dried and subsequently mixed with 1.2 g of magnesium stearate. From the granulate, tablets having about 60 to 500 mg of active substance are pressed, and these may be coated with a film of hydroxypropyl methyl cellulose. Likewise, film minitablets may be prepared and filled into capsules of solid gelatine.

EXAMPLE 5

Potassium Oxypurinol Tablets

A granulate according to example 4 is prepared using potassium oxypurinol or magnesium oxypurinol instead of the sodium salt. From this, tablets having appropriate therapeutical doses, preferably from 60 to 600 mg per tablet, may be pressed.

EXAMPLE 6

Oxypurinol in Serum after Peroral Application of Sodium Oxypurinol Tablets, and Tablets with micronized Oxypurinol, Respectively In an ordinary cross over design, 6 test persons each received 1 tablet having 384 mg of sodium oxypurinol and 336 mg of micronized oxypurinol, respectively. Blood samples were taken in usual narrow time intervals, and the oxypurinol concentration in the serum was determined. From the area below the serum level curve, the relative resorption rate was calculated. For the micronized oxypurinol preparation, this was 33% of that for sodium oxypurinol.

EXAMPLE 7

Oxypurinol in Serum after Peroral Application of Allopurinol and Sodium Oxypurinol Tablets, Respectively As in example 6, the course of the serum oxypurinol level and the areas below the curves after administration of 384 mg of sodium oxypurinol and 300 mg of allopurinol (standard gout therapeutic agent), respectively, were determined. The relative resorption rate of sodium oxypurinol as compared to oxypurinol from allopurinol was 87%.

EXAMPLE 8

Uric Acid Decreasing Effect of Sodium Oxypurinol Tablets

Each 10 test persons suffering from watery hyperuricaemia (serum uric acid 7.9±1.3 and 7.8±1.2 mg/100 ml, respectively) were given daily 384 mg of sodium oxypurinol and 300 mg of allopurinol, respectively, over a period of two weeks. In each group, there was an approximately equal decrease of the serum uric acid level by 2.1 and 2.0 mg/100 ml, respectively.

I claim:

1. An oral solid dosage form of a pharmaceutical composition comprising a pharmacologically effective amount of an oxypurinol salt, wherein the oxypurinol salt is an alkali salt, an alkaline earth salt, or a mixture thereof, in an amorphous or crystalline, non-micronized state, and a pharmaceutically acceptable carrier.

2. A pharmaceutical composition for the peroral treatment of hyperuricaemia comprising a pharmacologically effective amount of an oxypurinol salt, wherein the oxypurinol salt is an alkali salt, an alkaline earth salt, or a mixture thereof, in amorphous or crystalline non-micronized form and a pharmaceutically acceptable carrier, adjuvant, or mixture thereof wherein said composition is in a non-injectable form suitable for oral administration.

3. The composition of claim 2, wherein the pharmacologically effective amount is 50–500 mg.

4. The composition of claim 2, wherein the oxypurinol salt is an oxypurinol alkali salt.

5. The composition of claim 2, wherein the oxypurinol salt is an oxypurinol alkaline earth salt.

6. The composition of claim 2, wherein the oxypurinol salt is in amorphous non-micronized form.

7. The composition of claim 2, wherein the oxypurinol salt is in crystalline non-micronized form.

8. The composition of claim 2, wherein the oxypurinol salt is an oxypurinol alkali salt in amorphous non-micronized form.

9. The composition of claim 2, wherein the oxypurinol salt is an oxypurinol alkali salt in crystalline non-micronized form.

10. The composition of claim 2, wherein the oxypurinol salt is an oxypurinol alkaline earth salt in amorphous non-micronized form.

11. The composition of claim 2, wherein the oxypurinol salt is an oxypurinol alkaline earth salt in crystalline non-micronized form.

* * * * *